United States Patent [19]

Gales

[11] 4,084,426
[45] Apr. 18, 1978

[54] FOAM MONITOR AND METHOD

[75] Inventor: Peter W. Gales, Whitefish Bay, Wis.

[73] Assignee: Jos. Schlitz Brewing Company, Milwaukee, Wis.

[21] Appl. No.: 712,141

[22] Filed: Aug. 6, 1976

[51] Int. Cl.$^2$ ............................................. G01F 23/28
[52] U.S. Cl. ....................................... 73/60.1; 73/293; 250/577
[58] Field of Search .................... 73/60.1, 293, 290 V; 250/564, 573, 574, 577

[56] References Cited

U.S. PATENT DOCUMENTS

| | | | |
|---|---|---|---|
| 3,110,890 | 11/1963 | Westcott et al. | 73/290 V X |
| 3,454,759 | 7/1969 | Calhoun | 250/577 X |
| 3,713,338 | 1/1973 | Kind | 73/293 |

FOREIGN PATENT DOCUMENTS

| | | | |
|---|---|---|---|
| 765,577 | 8/1967 | Canada | 73/60.1 |
| 1,355,088 | 5/1974 | United Kingdom | 73/293 |

Primary Examiner—Richard C. Queisser
Assistant Examiner—Joseph W. Roskos
Attorney, Agent, or Firm—Andrus, Sceales, Starke & Sawall

[57] ABSTRACT

A foam monitor senses the dissipation of foam within a transparent tube and employs a series of vertically spaced light emitting diodes which are cyclically pulsed to provide repetitive sequential scanning of the tube contents and a series of photo-responsive elements are axially spaced along the diametrically opposite side of the tube and positioned to monitor corresponding intermittent light paths that may be received from the corresponding light emitting diodes. The intermittent light paths are monitored during each scanning cycle to provide a pulse train which is indicative of the relationship between scanned levels containing foam and scanned levels void of foam. The pulses produced over a predetermined number of repetitive scans are totalized to provide an analytical measurement of the foam dissipation qualities for the liquid involved.

15 Claims, 1 Drawing Figure

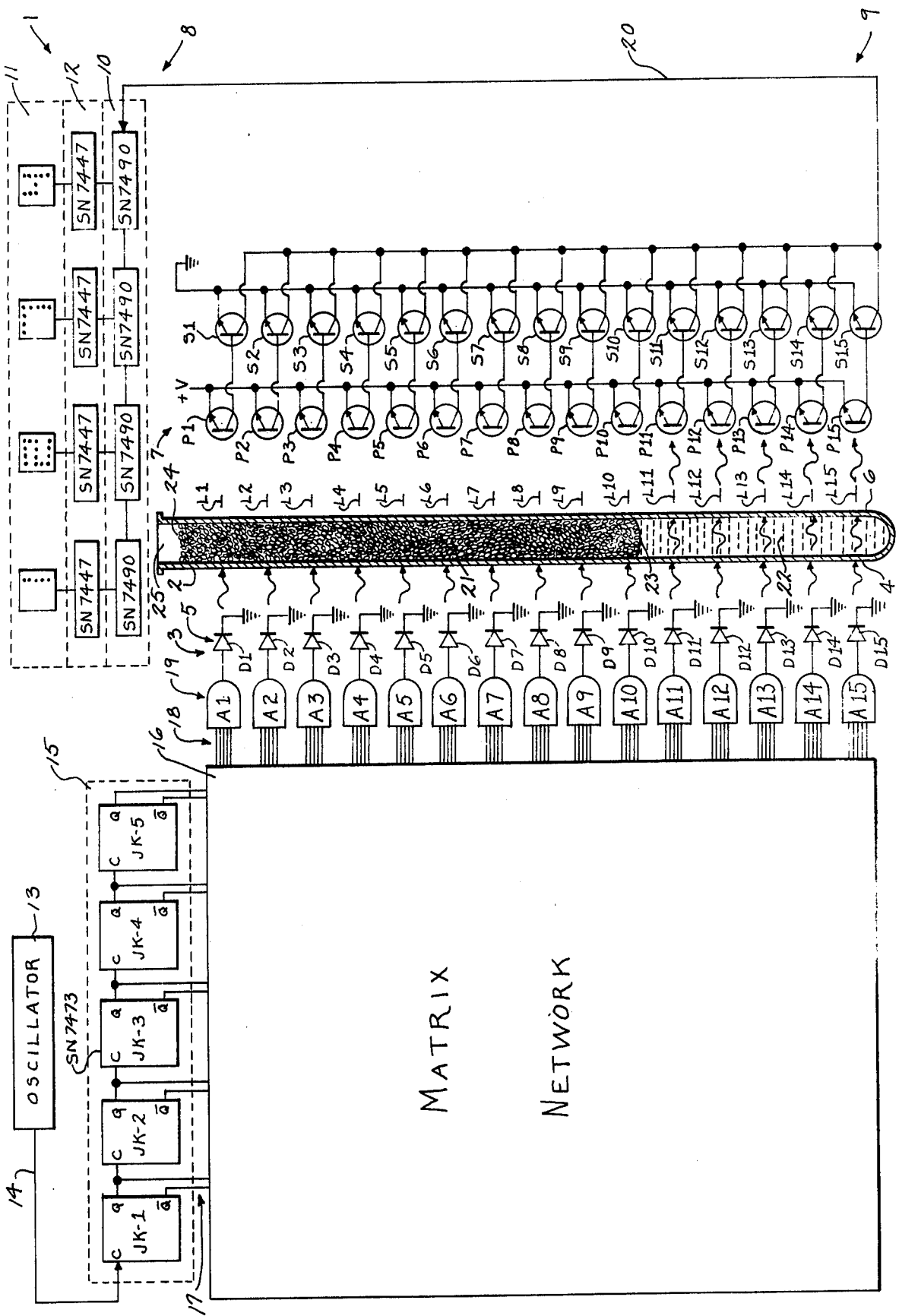

4,084,426

FOAM MONITOR AND METHOD

BACKGROUND OF THE INVENTION

This invention relates to a foam monitor and method of measuring the foam dissipation properties associated with a liquid.

The characteristics of foam formed between a liquid and a gas and particularly the foam dissipation properties is an important characteristic to be measured and possibly controlled for certain liquids, such as where liquids desirably contain dissolved or entrained gases. As an example, beer, which is a malted and hopped alcoholic beverage brewed by slow fermentation, generally contains dissolved and entrained gases, such as carbon dioxide, which may readily produce foam whenever pressure is rapidly reduced within its storage container or when it becomes agitated, such as when poured into a drinking container. The amount of foam generated or produced within a liquid such as beer may vary in accordance with its surface tension or elasticity and may be controlled through processing procedures concerning the formation of the liquid product.

In situations where foam is either a desirable or undesirable characteristic associated with a particular liquid product, it is advantageous to accurately monitor and record the foaming properties of the product, such as the dissipation rate of the foam. In such situation, it is desirable to accurately evaluate changes in foam stability and generate standards in terms of measured qualities to be used in evaluation of the liquid formation processes. Such monitored information may be helpful in suggesting modifications to the liquid formation processes in order to establish standard and uniform desirable foam characteristics of the liquid product.

SUMMARY OF THE INVENTION

This invention relates to a foam monitor and method of measuring the foam dissipation properties associated with a liquid.

In one aspect of the invention, a container retaining foam within an opening is scanned at a plurality of vertically spaced levels so that a first signal is generated for each scan level containing foam and a second signal is generated for each scan level void of foam. The first and second generated signals produced from the scan are monitored so that an output is provided which is responsive to the location of foam within the container.

The scan is operated by a control which sequentially and repetitively scans the series of container levels. The output provided by the foam monitor thus varies in response to the dissipation of the monitored foam.

In one form of the invention, scanning is provided by a plurality of sequentially actuated radiation sources located at spaced container levels along a first side wall of the container so that intermittent radiation paths are sequentially provided at spaced levels. A plurality of radiation sensors which correspond to the radiation sources are located along a second side wall portion of the container and particularly in a position so as to be capable of responding under certain conditions to the intermittent radiation paths provided by the corresponding radiation sources. In operation, each radiation sensor provides an output having a first condition in response to the presence of foam within the corresponding intermittent radiation path and a second condition in response to the dissipation of foam within the corresponding intermittent radiation path.

In one form of the invention, the radiation sources include a series of axially spaced light emitting sources located adjacent a first side of a transparent tube retaining liquid and foam wherein the liquid and foam form a first interface and the foam and liberated gas form a second interface with the first and second interfaces varying vertically in response to the dissipation of foam. Each light emitting source corresponds to a predetermined level of the transparent tube and operatively provides a series of intermittent light paths at the predetermined level. The light emitting sources are repetitively supplied intermittent energizing power in a sequential manner so as to operatively provide intermittent light paths in a cyclical pattern to the transparent tube. The radiation sensors include a series of axially spaced photoresponsive elements which are adjacent a second side of the transparent tube so as to be diametrically opposed or opposite to the series of light sources and positioned to respond to the sequentially and repetitively actuated intermittent light paths at the predetermined levels. In such a construction, each photoresponsive element operates to produce a first output in response to foam within its associated intermittent light path and a second output in response to the dissipation of foam within its associated intermittent light path. The plurality of first and second outputs provided by or generated from the outputs of the photo-responsive elements are formed into a pulse train indicative of the amount of foam within the tube.

The pulses produced from the output of the scan may be accumulated to form a count in a pulse counter to provide an output varying in response to the status of the foam. In a preferred form of the invention, a decimal output indication is provided by an indicator which is operatively connected to respond to the accumulated pulse count within the pulse counter.

The sequence control which operates the scan employs a series of oscillator controlled flip-flops providing a plurality of sequential and repetitive binary coded outputs. With such construction, each of the radiation emitters is operatively connected to the binary coded outputs through a matrix circuit and operatively respond to a preselected binary coded output to provide an intermittent radiation pulse. Such radiation emitting sources are connected to the matrix circuit through a logic circuit, such as a logic AND circuit for example, which responds only to the preselected binary coded output.

A method of measuring the foam dissipation properties of a liquid is also provided by the invention. In one form, foam is placed in a container which is repetitively scanned at a plurality of spaced container levels to provide for each scanning cycle a series of output signals indicative of the relationship between scanned levels containing foam and scanned levels void of foam. A count is accumulated of such output signals during a predetermined time period of repetitive scans to provide an indication of the foam dissipation properties of the liquid.

In another form of the invention, foam is placed in a container which is cyclically scanned at a plurality of spaced container levels to provide an output signal for each scan level void of foam. A count is accumulated of such output signals during a predetermined period of time to provide an indication of the foam dissipation properties of the liquid.

The invention provides a unique monitor and method of responding to foam to provide a quantitative measurement which is extremely valuable in evaluating changes in foam stability.

BRIEF DESCRIPTION OF THE DRAWINGS

The drawing furnished herewith illustrates the best mode presently contemplated by the inventor and clearly discloses the above advantages and features as well as others which will be readily understood from the detailed description thereof.

In the drawing:

The FIGURE represents an electrical schematic and diagrammatic view of a foam dissipation monitor.

DESCRIPTION OF THE PREFERRED ILLUSTRATED EMBODIMENT

Referring to the drawing, a foam dissipation monitoring system 1 senses the dissipation of foam within a transparent tube 2 which may consist of an elongated cylindrical tube such as made of glass, for example. A radiation source 3 is positioned adjacent a first side 4 of tube 2 and includes fifteen light emitting diodes (LEDs) 5 designated D1 through D15, inclusive, which are axially spaced along the side wall 4 and in close proximity to tube 2. The LEDs 5 are axially spaced so as to be located at predetermined levels of tube 2 which are indicated along side wall 6 by the designations L1 through L15, inclusive, indicating fifteen axially spaced levels corresponding to the positioning of the LEDs D1 through D15 along the side wall 4. When energized, the LEDs 5 provide a source of radiant energy directed toward tube 2 at side wall 4 so that a light path is formed along each level corresponding to the LEDs D1 through D15. Although not shown, an optical lens is placed between each of the LEDs and the tube 2 for forming a beam of substantially parallel radiant energy rays at the associated level.

A series of radiation sensors 7 are axially spaced along the side wall 6 of tube 2 and are shown located diametrically opposite to the series of LEDs 5. The radiation sensors 7 are designated P1 through P15, inclusive, and correspond to the fifteen LEDs 5 designated D1 through D15, respectively. The individual radiation sensors P1 through P15 are located in close proximity to the tube 2 and axially spaced to correspond to the series of levels designated L1 through L15, respectively, which have been defined by the positioning of the diodes D1 through D15, respectively.

The radiation sensors 7 are electrically connected to an output monitor 8 through a coupling circuit 9, the latter providing a series of switching transistors designated S1 through S15, inclusive, with each switching transistor electrically connected to a respective associated radiation sensor P1 through P15. The output monitor 8 includes a decade counter 10 which is electrically coupled to a series of seven segment visible decimal readouts 11 through a series of BCD-to-seven-segment decoders and drivers 12.

The radiation source 3 includes an oscillator 13 which may constitute a commercially available astable multivibrator capable of free running operation or any other type of electrical oscillating circuit which provides an oscillatory output at 14. Although not absolutely necessary, it is desirable to provide a substantially square wave constant frequency output signal at 14 to be supplied to a series of interconnected J-K flip-flops at 15. The series of flip-flops 15 may be interconnected to operate in a manner similar to a ripple counter. While a variable number of J-K flip-flops may be interconnected to provide, in effect, a ripple counter sequence of operation, the preferred embodiment employs five J-K flip-flops which have been designated JK-1 through JK-5, inclusive. The flip-flops JK-1 through JK-5 are interconnected in series so that the Q output of the first four flip-flops JK-1 through JK-4 are connected to the clock inputs of the next succeeding JK flip-flops JK-2 through JK-5 and are further connected to supply five outputs to a matrix network 16. The $\overline{Q}$ outputs for the flip-flops JK-1 through JK-5 are also connected to supply outputs to the matrix network 16. Thus, a series of outputs as indicated at 17 are supplied from the J-K flip-flops 15 to the matrix circuit 16.

The matrix network 16 may constitute a commercially available ROM which is capable of accepting at least 10 inputs and supplying at least 75 or more outputs and capable of being selectively programmed to respond to the cyclically changing binary signals supplied at output 17 to thereby supply predetermined outputs at the output circuits shown at 18. The radiation source 3 further includes a series of logic AND gates 19 which have been designated A1 through A15, inclusive, and which provide fifteen separate outputs connected to an associated LED, namely D1 through D15, respectively. Each AND gate at 19 includes five input circuits which are connected to five predetermined output leads at 18 provided by the matrix 16. Pre-programming of the matrix 16 is accomplished by establishing an electrical circuit between a particular output lead 18 connected to a particular AND gate 19 and a particular output lead at 17 provided by the series of flip-flops 15. Such interconnection may be made directly or through steering diodes provided by the matrix 16.

In operation, each AND gate A1 to A15 will provide a logic "1" or high signal level output only when all five inputs are at a logic "1" or high signal level. Such a logic "1" or high output from a particular AND gate such as A1, for example, is effective to energize an associated LED 5, namely LED D1 associated with gate A1. Specifically, the AND gate A1 will respond to logic "1" signals at all five inputs to provide a logic "1" output to the LED D1 thereby providing a radiation path at level L1. The occurrence of a logic "0" or low signal level at any one input to gate A1 will produce a logic "0" or low signal level output to the LED D1 to thereby de-energize such LED and extinguish the radiation path at level L1.

The light sensors 7 designated as P1 through P15 may each include an NPN type silicon photo-transistor. Such series of photo-transistors are positioned and interconnected so that their light sensitive base materials will be facing one of the appropriate light paths L1 – L15. Each of the photo-transistors P1 – P15 provides an emitter circuit connected to a constant potential voltage source +V and a collector circuit connected to the coupling circuit 9 and particularly to a base input circuit of an associated switching transistor S1 through S15, respectively. The transistors S1 through S15 may each consist of an NPN type switching transistor which has an emitter circuit connected to a system neutral or ground and a collector circuit connected to the output monitor 8. Specifically, each collector output circuit provided by the switching transistors S1 through S15 are connected in common to an output lead 20 which, in turn, is connected as an input to the decade counter 10. The decade counter 10 may consist of a series of commercially available counter elements such as supplied by Texas Instruments and designated SN7490. Although only four decade counter elements SN7490 are shown, any number may be employed to accommodate the anticipated pulse count required for normal operations of the foam dissipation monitor 1. The output of each decade counter module, which may constitute a four-lead output providing a binary coded signal, is supplied as an input to a BCD-to-seven-segment decoder and driver 12 which may be selected from a commercially available component such as provided by Texas Instruments under the designation SN7447. Each decoder at 12 thus receives four input circuit leads providing a binary coded signal and provides seven output circuits which are interconnected to drive a seven-segment visible read-out 11.

In operation, a foam dissipation test sequence is initiated by filling the tube 2 with foam or froth involving a particular liquid. As an example of one possible operation in the beer brewing industry, the beer undergoing a foam dissipation test may rapidly be poured into tube 2 so that the tube is substantially filled with foam while only a small lower portion of the tube will contain clear liquid beer. The oscillator 13 is thereafter activated to supply a series of constant frequency pulses to the flip-flops 15. The flip-flops 15 respond to the input of constant frequency pulses and provide a constantly changing output to the matrix network 16 which constitutes a cyclically changing binary output similar to that commonly experienced from ripple counters. The matrix 16 is pre-programmed so that the AND gates 19 and associated LEDs 5 are sequentially and intermittently energized to provide a scanning sequence. As an example, the AND gate A1 will be energized only for one cycle of the input frequency of oscillator 13 and thereafter be de-energized while the next succeeding AND gate A2 will be energized for the next succeeding cycle of input frequency. Thus, only one LED 5 will be intermittently energized at any one time and the series of LEDs D1 through D15 will be sequentially energized in a scanning pattern which will be cyclically repeated as long as oscillator 13 continues to operate.

The radiation source 3 will thus sequentially scan the contents of the tube 2 by sequentially energizing the LEDs 5. Over a given period of time, the foam as at 21, such as involved with beer in the present illustrated example, will gradually dissipate so that the liquid as illustrated at 22 will increase thereby causing the foam-liquid interface 23 to rise in tube 2. The gradual dissipation of foam 21 in tube 2 will also cause the lowering of an interface 24 existent between the foam 21 and a column of air 25 in tube 2. The illustrated drawing represents a particular foam dissipation state wherein the amount of liquid, such as beer, has increased through the dissipation of foam so that the interface 23 is between levels L10 and L11. Because of the clinging properties of foam, the foam-air interface 24 varies only slightly and generally remains above the upper level L1 during a testing sequence. In such a situation as diagrammatically illustrated in the drawing, the intermittent radiation rays produced by LEDs D11 through D15, inclusive, pass through the column of beer 22 thereby activating the radiation sensors P11 through P15. The bubbles within the foam or froth at 21, however, will reflect, refract or absorb the intermittent radiation rays provided by the LEDs D1 through D10, inclusive, so that the radiation sensors P1 through P10 will not be activated. Thus, in a scanning sequence for a state of foam dissipation as illustrated in the drawing, the switching transistors S11 through S15 will be intermittently operated in sequence while the switching transistors S1 through S10 will remain inoperative.

In that the switching transistors S1 through S15 are sequentially and selectively operated, the combined output at 20 will constitute a train of pulses, the number of which will provide an indication of the state of foam dissipation within tube 2 during a particular scan cycle. The decade counters 10 will count and totalize the pulses within the train supplied at output 20 and provide an output to the display 11 which reflects the running totalized count of all received pulses.

As the foam continues to dissipate, the interface 23 will rise so that additional photo-transistors such as P10 will be subsequently actuated thereby increasing the number of output pulses during each scanning cycle. While a testing sequence is generally not of a duration to permit the descent of the interface 24 to the level L1, it is contemplated that the invention could also function with the foam-air interface 24 decreasing to a level below L1 thereby permitting additional photo-transistors to be actuated, such as P1 for example, and likewise increase the number of output pulses during each scanning cycle.

An increased rate of foam dissipation will thereby result in an increased number of output pulses during subsequent scanning cycles and thereby increase the pulse count in counter 10 at a more rapid rate. By operating the foam dissipation monitoring sequence over a predetermined period of time, the pulses from a predetermined number of scanning cycles will be accumulated and counted to provide an analytical measurement for comparison with pre-established acceptable foam dissipation standards for the liquid involved. Although a timer is not shown in the illustrated drawing, a conventional timer may be interconnected to operate automatically in response to the operation of the foam dissipation monitor 1 or a hand-held stop watch may be employed to establish predetermined time durations for monitoring the foam dissipation count accumulated within the registers 10 and displayed at the read-out 11. In operation in the beer industry, various brews of beer may be comparatively analyzed to determine whether particular brews have the requisite foam dissipation qualities.

Various modes of carrying out the invention are contemplated as being within the scope of the following claims particularly pointing out and distinctly claiming the subject matter which is regarded as the invention.

I claim:

1. A foam monitor, comprising a container having an opening retaining a foam, means scanning said container opening at a plurality of vertically spaced levels and providing a first signal for each scanned level containing foam and a second signal for each scanned level void of foam, and means responding to said first and second signals provided by said scanning means and providing an output responsive to the dissipation of foam and indicative of the state of foam dissipation within said container.

2. The foam monitor of claim 1, wherein said scanning means includes control means sequentially and repetitively scanning said container levels, and said output of said output means varying in response to the dissipation of said foam.

3. A foam monitor, comprising a container having an opening retaining a foam, means scanning said container opening at a plurality of vertically spaced levels and including control means sequentially and repetitively scanning said container levels and providing a first signal for each scanned level containing foam and a second signal for each scanned level void of foam, and means responding to said first signals provided by said scanning means and providing an output varying in response to the dissipation of said foam within said container and including circuit means combining said first and second signals and forming a pulse train at said output.

4. The foam monitor of claim 3, wherein said output means includes a pulse counter responding to said pulse train and accumulating a count varying in response to the dissipation of said foam.

5. The foam monitor of claim 4, wherein said output means includes an indicator operatively connected to said pulse counter and providing a decimal output indication correlated to the accumulated pulse count in said counter.

6. A foam monitor, comprising a container having an opening retaining a foam, means scanning said container opening at a plurality of vertically spaced levels and including control means sequentially and repetitively scanning said container levels and providing a first signal for each scanned level containing foam and a second signal for each scanned level void of foam, said scanning means including a series of spaced radiation emitters proximate to said container and sequentially and intermittently energized by said control means to provide sequential radiation pulses to said container opening, and means responding to said first and second signals provided by said scanning means and providing an output varying in response to the dissipation of said foam within said container.

7. The foam monitor of claim 6, wherein said control means includes a series of oscillator controlled flip-flops providing a plurality of sequentially changing binary coded outputs, each of said radiation emitters operatively connected to said binary coded outputs through a matrix circuit and operatively responding to a preselected binary coded output to provide an intermittent radiation pulse.

8. The foam monitor of claim 7, wherein each of said radiation emitters is operatively connected to said matrix circuit through an AND logic circuit.

9. A foam monitor, comprising a container having an opening retaining a foam, an energy source providing radiation into said container opening, first and second spaced sensors located at first and second spaced levels, respectively, of said container and each sensor responsive to said radiation and having an output operatively providing a first condition in response to the presence of foam at said corresponding level and a second condition in response to the dissipation of foam at said corresponding level, and means responding to continuous monitoring of said first and second sensor outputs and providing an output responsive to the dissipation of foam and indicative of the state of foam dissipation within said container.

10. The foam monitor of claim 9, wherein said container includes a transparent tube, and said energy source includes first and second radiation emitters axially spaced along a first side wall of said container and positioned approximately at said first and second container levels, respectively, for selectively providing first and second radiation paths into said container opening.

11. A foam monitor, comprising a container retaining a foam between first and second spaced side wall portions, means supplying radiation at said first side wall portion and including a plurality of sequentially actuated radiation sources located at corresponding spaced container levels and sequentially providing intermittent radiation paths at said spaced levels, means sensing radiation at said second side wall portion and including a plurality of radiation sensors corresponding to said radiation sources and responding to said intermittent radiation paths with each sensor having an output operatively providing a first condition in response to the presence of foam within the corresponding intermittent radiation path and a second condition in response to the dissipation of foam within the corresponding intermittent radiation path, and means responding to said plurality of sensor outputs and providing an output responsive to the dissipation of foam within said container.

12. A foam monitor, comprising a transparent tube retaining liquid and foam wherein said liquid and foam forms a first interface and said foam and liberated gas forms a second interface with said first and second interface varying vertically in response to the dissipation of foam, a series of axially spaced light emitting sources located adjacent a first side of said tube with each source corresponding to a predetermined level for said tube and operatively providing a series of intermittent light paths each corresponding to a predetermined level, means operatively connected to said series of light sources and repetitively supplying in sequence intermittent energizing power to said light sources and operatively providing said intermittent light paths in a sequential and repetitive pattern, a series of axially spaced photo-responsive elements adjacent a second side of said tube diametrically opposite to said series of light sources and positioned to respond to said sequentially and repetitively actuated intermittent light paths at said predetermined levels, each of said photo-responsive elements operating to produce a first output in response to foam within its associated intermittent light path and a second output in response to the dissipation of foam within its associated intermittent light path, means responding to said plurality of first and second element outputs and producing a pulse train indicative of the amount of foam within said tube, and means responding to said pulse train and providing an output indication responsive to the dissipation of foam within said tube.

13. The foam monitor of claim 12, wherein said energizing means includes a plurality of oscillator controlled flip-flops providing a plurality of sequential and repetitive binary coded outputs to a matrix circuit and each of said light emitting sources connected to said matrix circuit through a logic circuit responding only to a preselected binary coded output to provide intermittent light paths, and said pulse train responsive means includes a pulse counter operatively accumulating a count varying in response to the foam dissipation and providing a binary coded output to a decimal output indicator through a binary to decimal code converter.

14. A method of measuring the foam dissipation properties associated with a liquid, comprising the steps of placing foam in a container, repetitively scanning a plurality of spaced container levels and providing for each scanning cycle a series of output signals indicative of the relationship between scanned levels containing foam and scanned levels void of foam, and accumulating a count of said output signals during a predetermined time period of repetitive scans for providing an indication of the foam dissipation properties associated with the monitored liquid.

15. A method of measuring the foam dissipation properties associated with a liquid, comprising the steps of placing foam in a container, cyclically scanning a plurality of spaced container levels and providing an output signal for each scanned level void of foam, and accumulating a count of said output signals during a predetermined period of time for providing an indication of the foam dissipation properties associated with the monitored liquid.

* * * * *